(12) United States Patent
Vaccaro et al.

(10) Patent No.: US 7,424,818 B2
(45) Date of Patent: Sep. 16, 2008

(54) ULTRASONIC INSPECTION REFERENCE STANDARD FOR POROUS COMPOSITE MATERIALS

(75) Inventors: Christopher M. Vaccaro, Ofallon, MO (US); David Lilienthal, Kent, WA (US)

(73) Assignee: Boeing Company, Chicago, IL (US)

( * ) Notice: Subject to any disclaimer, the term of this patent is extended or adjusted under 35 U.S.C. 154(b) by 207 days.

(21) Appl. No.: 11/254,464

(22) Filed: Oct. 20, 2005

(65) Prior Publication Data

US 2007/0089479 A1    Apr. 26, 2007

(51) Int. Cl.
*G01M 1/14*    (2006.01)
(52) U.S. Cl. ........................................................ 73/1.86
(58) Field of Classification Search ................ 73/1.38, 73/618, 1.86, 620, 1.03, 1.82; 204/192.13
See application file for complete search history.

(56) References Cited

U.S. PATENT DOCUMENTS

| | | | | |
|---|---|---|---|---|
| 4,674,334 | A * | 6/1987 | Chimenti et al. | 73/627 |
| 5,127,268 | A * | 7/1992 | Kline | 73/597 |
| 5,238,556 | A * | 8/1993 | Shirkhan | 210/198.2 |
| 5,637,175 | A * | 6/1997 | Feygin et al. | 156/264 |
| 6,684,701 | B2 * | 2/2004 | Dubois et al. | 73/579 |
| 2002/0197834 | A1 * | 12/2002 | Asakawa et al. | 438/584 |
| 2003/0217599 | A1 * | 11/2003 | Peterson et al. | 73/602 |
| 2006/0213250 | A1 | 9/2006 | Vaccaro et al. | |
| 2006/0257781 | A1 * | 11/2006 | Benoit et al. | 430/270.1 |

FOREIGN PATENT DOCUMENTS

| | | | |
|---|---|---|---|
| GB | 2221991 A | * | 2/1990 |
| JP | 08210953 A | * | 8/1996 |

OTHER PUBLICATIONS

Rose et al., "Ultrasonic Computed Tomography Considerations in NDE of Solid Materials", Dec. 1990, Ultrasonics Symposium, Preceedings., IEEE 1990,991-995.*

* cited by examiner

*Primary Examiner*—Hezron Williams
*Assistant Examiner*—Tamiko Bellamy
(74) *Attorney, Agent, or Firm*—Wildman, Harrold, Allen & Dixon, LLP

(57) ABSTRACT

An ultrasonic inspection reference standard for composite materials having porosity may include a member, having at least one thickness and defined by a plurality of holes, that is manufactured from a fiber-free polymer resin. The ultrasonic inspection reference standard may have similar acoustic properties to prior art, porous, fiber-reinforced, composite reference standards, at lower manufacturing cost. A photopolymer resin reference standard, having at least one thickness and defined by a plurality of holes, may be created using a stereo lithography process. The polymer resin reference standard may replace more costly porous, fiber-reinforced, composite reference standards. The ultrasonic inspection reference standard, manufactured from a polymer resin, may be used for ultrasonic inspection of porous, fiber-reinforced composite parts in the aircraft industry and in other non-aircraft applications.

24 Claims, 9 Drawing Sheets
(6 of 9 Drawing Sheet(s) Filed in Color)

ULTRASONIC INSPECTION REFERENCE STANDARD FOR POROUS COMPOSITE MATERIALS

CROSS-REFERENCE TO RELATED APPLICATIONS

This application hereby incorporates by reference U.S. application Ser. No. 11/090,553, filed on Mar. 25, 2005, and titled Ultrasonic Inspection Reference Standard For Composite Materials.

BACKGROUND OF THE INVENTION

Composite laminate reference standards are employed when performing ultrasonic inspection on composite laminate materials. They are used to aid in the detection of planer defects such as denominations, foreign material, and the detection and quantification of porosity. A relationship exists between the strength of a composite laminate and the presence of defect conditions. This relationship is established in the course of effects-of-defects programs that look at the strength degradation of materials as a result of defects. Composite reference standards are currently manufactured with representative planer conditions to aid in the detection of denominations and foreign material. It is difficult however to tie detection and quantification of porosity to a representative planer defect reference standard without the introduction of defects that mimic porosity.

Due to this difficulty, one approach to detecting and quantifying porosity in composite laminates has been to build a set of porosity reference standards for a given material. This set of standards, which are costly to build and certify for use, are used to qualify production inspection systems and are used to determine the operating characteristics of ultrasonic inspection systems. The introduction of new composite materials and the cost associated with qualifying new and existing ultrasonic inspection systems to inspect those materials has produced a need to build and qualify less expensive porosity standards. The standards, once produced, can be tied back to material properties via effects-of-defects programs and used to evaluate the strength characteristics of the materials being inspected.

SUMMARY OF THE INVENTION

In one aspect of the present invention, an ultrasonic inspection reference standard for composite materials having porosity comprises a member having at least one thickness. The member is defined by a plurality of holes and manufactured from a fiber-free polymer resin.

In another aspect of the present invention, an ultrasonic inspection reference standard for composite materials having porosity comprises a member having at least one thickness. The member is manufactured from a fiber-free polymer resin using stereo lithography, and is adapted to contain the acceptable or respectable ultrasonic properties of a fiber-reinforced composite part having porosity.

In a further aspect of the present invention, an ultrasonic inspection process for composite materials having porosity comprises the steps of: manufacturing an ultrasonic inspection reference standard defined by a plurality of holes from a fiber-free polymer resin; and inspecting a fiber-reinforced composite part having porosity with an ultrasonic technique using the fiber-free polymer resin reference standard defined by a plurality of holes.

These and other features, aspects and advantages of the present invention will become better understood with reference to the following drawings, description and claims.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Figure 1:
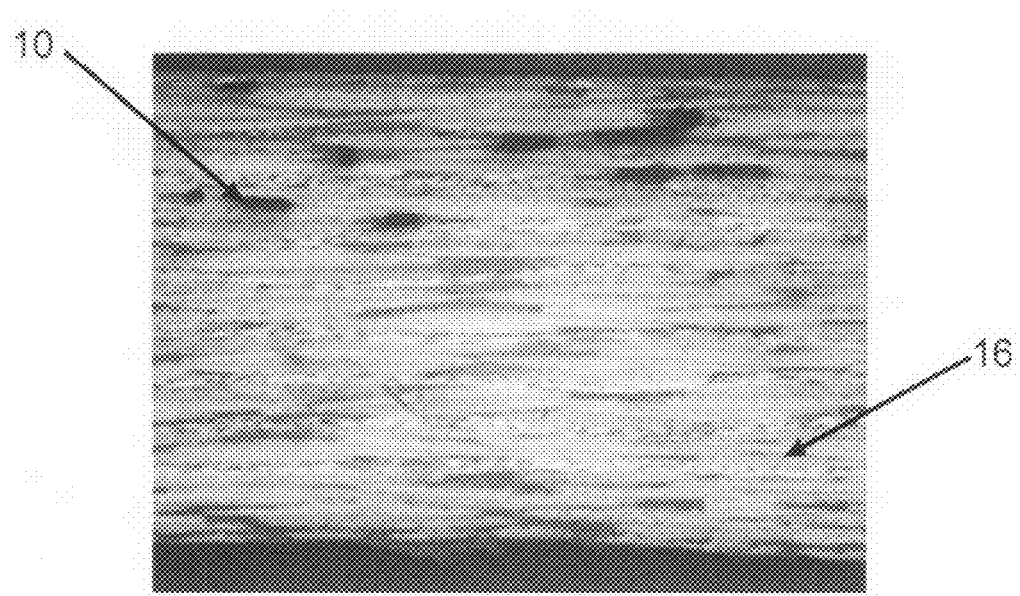
FIG. 1 is a photomicrograph of a composite laminate with porosity.
Figure 2:
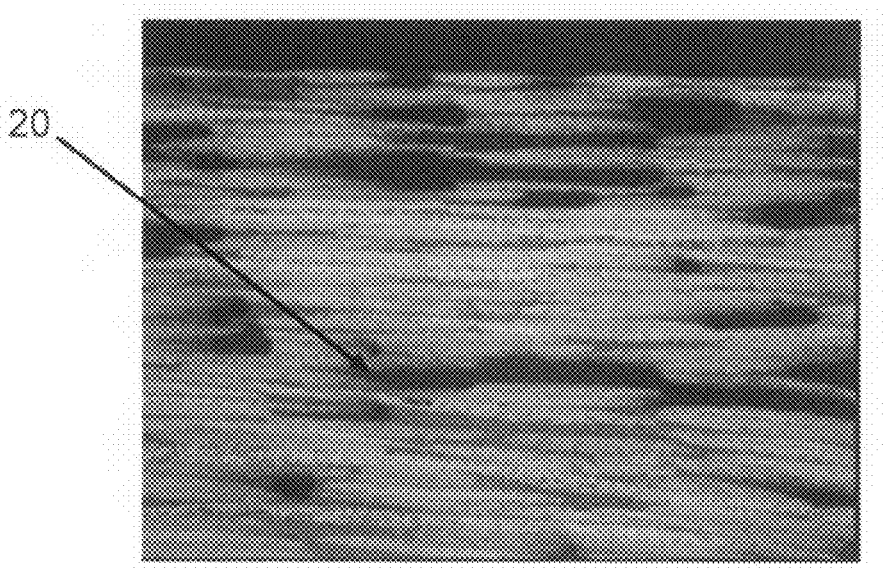
FIG. 2 is a photomicrograph of a composite laminate with large, planer-like porosity.

Composite laminates consist of two primary constituents including a fiber, and a resin matrix that bonds the fibers together. The fiber is typically graphite. Porosity in composite laminates is an unwanted product of the manufacturing cure cycle and is characterized by voids or a lack of resin within the laminate. FIG. 1 depicts a photomicrograph of a composite laminate with areas of high porosity 10 shown as elliptical shapes that appear darker than the surrounding non-porous areas 16. The morphology and distribution of the porosity vary depending on a number of processing variables. The size of porosity also varies from relatively small diameters of 0.005' up to large planer conditions 20 like those illustrated in FIG. 2.

Figure 3:
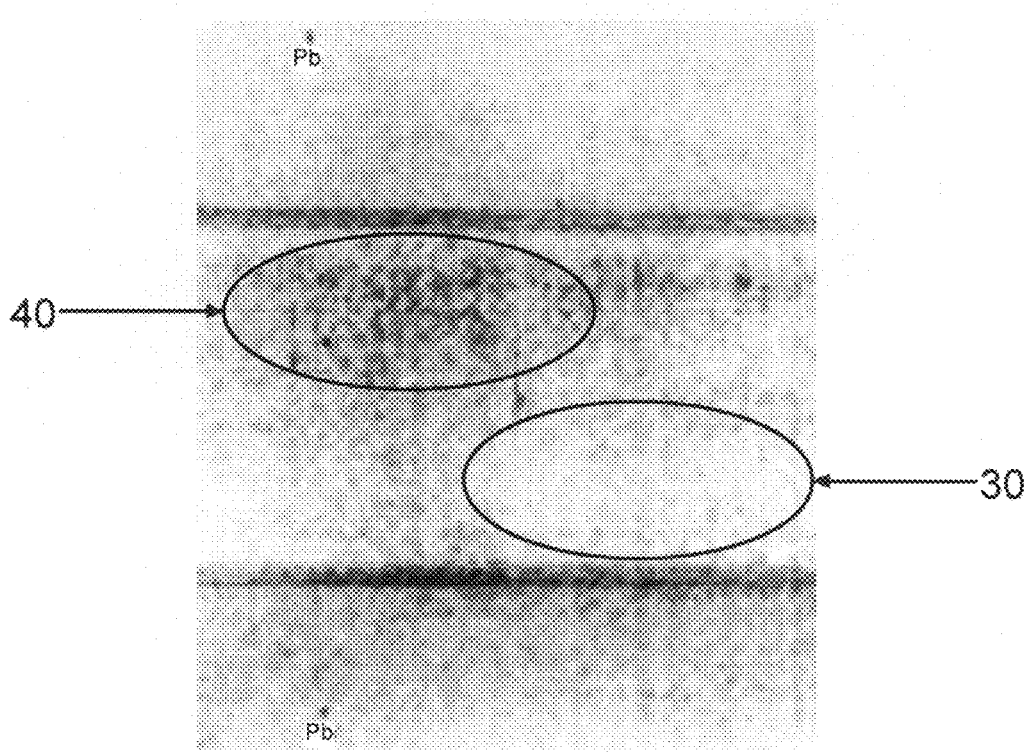
FIG. 3 is an ultrasonic C-scan of a composite laminate with porosity.

Porosity within a composite laminate may be quantitatively measured using high frequency ultrasonic methods. As the void content of a laminate increases, so does the ultrasonic attenuation. Ultrasonic attenuation is the combined loss of acoustic energy within the laminate which results from reflection and scattering of the sound pulse as it passes through the laminate. The ultrasonic C-scan in FIG. 3 illustrates this condition. The light gray areas 30 are where there is very little to no porosity in the laminate. The dark areas are where the laminate has porosity of some level.

Previous work has shown that photo-polymer resins used in stereo lithography (SLAB), as well as conventional thermos set and thermoplastic resins like those used to bind fibers in composite laminates, have similar ultrasonic (acoustic) properties to graphite epoxy composite laminates. This is detailed in U.S. application Ser. No. 11/090,553, filed on Mar. 25, 2005, and titled Ultrasonic Inspection Reference Standard For Composite Materials, which is hereby incorporated by reference.

Figure 4:
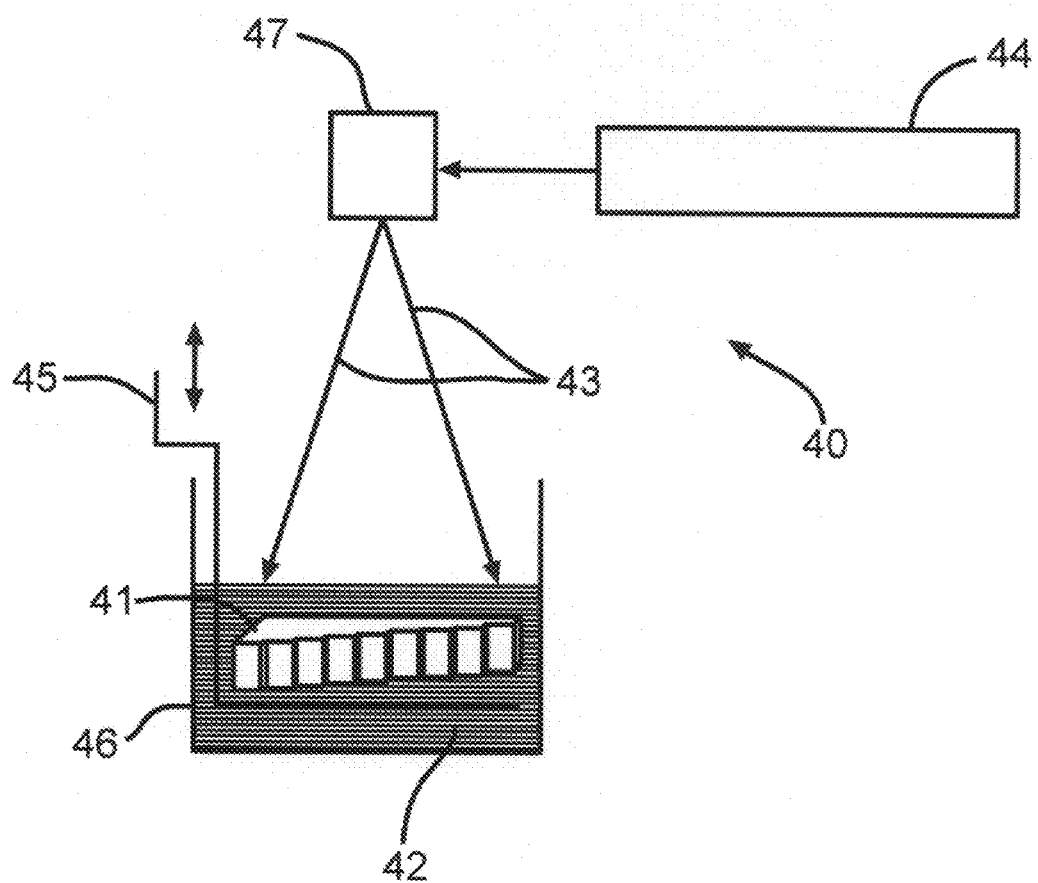
FIG. 4 is a front view of a stereo lithography process.

As shown in FIG. 4, the use of a stereo lithography process 40 may produce plastic parts 41, such as an ultrasonic inspection reference standard manufactured from a photo-polymer resin, directly from a 3D CAD (computer-aided design) model. The surface of a liquid photo polymer 42 is solidified layer-by-layer using a laser beam 43 emitted by a laser 44. When the laser beam 43 hits the liquid photo polymer 42, it solidifies the resin. When a layer is fully traced, a movable table 45 is than lowered in the vat 46. A scanner system 47 directs the laser beam 43 according to a loaded CAD model. The self-adhesive property of the material causes the layers to stick with each other and in this way a three-dimensional part 41 is formed in multi-layers. The stereo lithography process 40 is accurate and suitable for smooth surface finished parts. Parts manufactured using the stereo lithography process 40 may be used, for example, for conceptual designs, product verification, pattern making. The stereo lithography process 40 may be used, for example, for rapid prototyping. Use of the stereo lithography process 40 may enable the manufacture of ultrasonic inspection reference standards, such as a polymer resin reference standard, with varying thicknesses and geometries that resemble the fiber-reinforced part to be inspected. The method of manufacturing an ultrasonic inspection reference standard from a fiber-free polymer resin may not require any tooling, and is not limited to the methods discussed.

To demonstrate the use of a fiber-free photo-polymer resin as a reference standard, a photo-polymer resin reference standard was manufactured with the same physical steps as a prior art graphite-epoxy reference standard by using the stereo lithography process 40 shown in FIG. 4. Both standards were then ultrasonic ally scanned at 5.0 MHz using both the through-transmission technique and the pulse-echo technique. The obtained data for the through-transmission technique is illustrated in the x-y plot 50 of FIG. 5, while the obtained data for the pulse-echo technique is illustrated in the x-y plot 60 of FIG. 6. The plots demonstrate attenuation 52 and 62 measured in decibels (dB) versus thickness 51 and 61 measured in inches. The attenuation is a decrease in intensity of a sound wave as a result of absorption and scattering of ultrasonic energy. The plots 50 and 60 include data points 63 and 63 for a photo-polymer resin reference standard free of fibers, and data points 54 and 64 obtained for a prior art graphite-epoxy reference standard.

Figure 5:
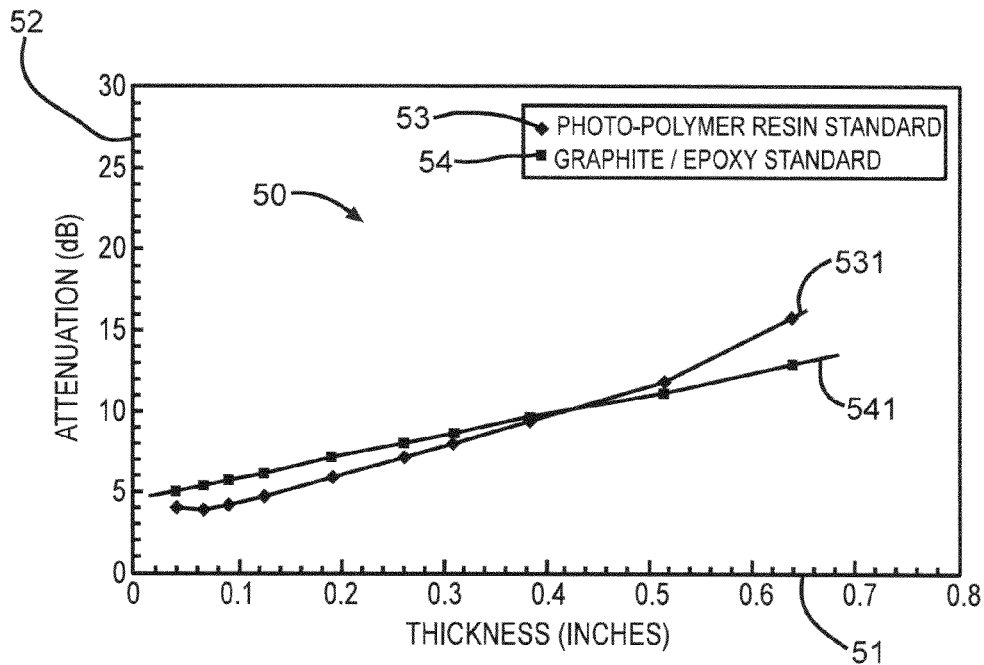
FIG. 5 is an x-y plot showing attenuation versus thickness applying through-transmission technique to both a photo-polymer resin standard and a graphite-epoxy standard.
Figure 6:
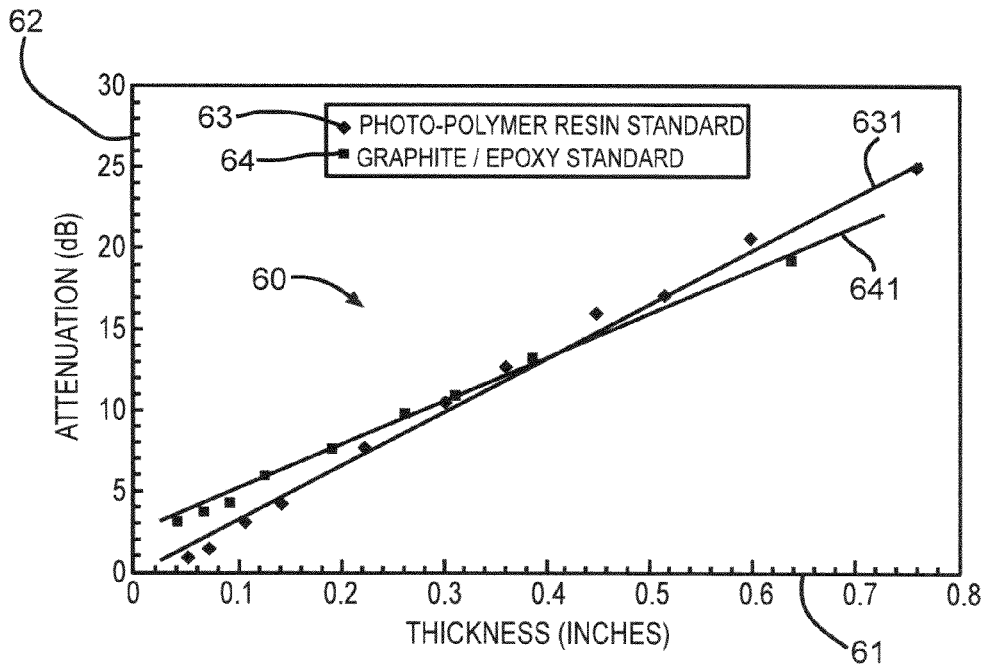
FIG. 6 is an x-y plot showing attenuation versus thickness applying pulse-echo technique to both a photo-polymer resin standard and a graphite-epoxy standard.

As shown in FIGS. 5 and 6, the slopes 531 and 631 of the photo-polymer resin standard is steeper than the slopes 541 and 641 of the prior art graphite-epoxy reference standard. However, the results are within the system noise, which is typically +/−2 dB. Consequently, the prior art graphite-epoxy reference standard may be substituted with the photo-polymer resin reference standard that is fiber-free. Since ultrasonic attenuation is material dependent, altering the thickness of the polymer resin reference standard may be used to bring the slopes 531, 541, 631, and 641 in line if needed. Using this approach, a fiber-free polymer resin reference standard may be designed to have an equivalent thickness based on the material properties of the fiber-reinforced composite part to be tested and not the actual thickness of a prior art fiber-reinforced composite reference standard.

The present invention makes use of stereo lithography and photo polymer resin to produce holes or voids in solid laminates of the size and morphology seen in composite laminates with porosity. In other embodiments, any type of fiber-free polymer resin may be used, including the use of a polymer resin which is identical to the resin of a composite material to be inspected. In still other embodiments, a non-stereo lithography process may be applied. Alternate methods of producing such holes, such as drilling and stamping, may be difficult to control, costly to produce, and may not produce holes of the size necessary to mimic porosity.

In one embodiment of the invention, the process starts with building a three-dimensional model with holes of the desired size. The model, which may be arrived at using computer-aided-drafting, is loaded into a stereo lithography machine for curing with a laser. The stereo lithography process, with its high degree of precision, can produce hole diameters approaching the laser diameter of 0.005". This is dependent on a number of variables including the size of the laser, the laser power rating, and the resolution of the scanning platform. In curing the photo polymer resin, the laser rasters back and forth curing resin only in the areas where the solid model indicates material to be. Areas like holes, cavities, and recessed areas that are not cured by the laser burst are subsequently flushed to remove the resin.

Once produced, the sample, which comprises a member having at least one thickness, is removed from the stereo lithography chamber for post cure using UV light. The member may comprise any shape, configuration, or thickness. The thickness of the member may be a substantially equivalent thickness based on the material properties of the composite material to be inspected. A combination of low viscosity of the resin and capillary action prevents the resin from being released from the small cavities like those molded after porosity. Prior to the UV cure, the sample must be worked to remove any uncured resin from the holes. This may be accomplished by removing the resin with compressed air or by plunging the cavities with a small instrument like a wire or drill. The process produces an ultrasonic reference standard, made of fiber-free polymer resin, containing a plurality of holes in the reference standard. The holes substantially mimic the ultrasonic properties of a porous composite material, allowing the replacement of fiber-reinforced composite reference standards. A varying amount of attenuation, or porosity, may be produced in any given member to produce the desired ultrasonic reference standard. The produced member, or standard, may contain the acceptable or respectable ultrasonic properties of the porous, composite materials to be inspected, to allow a decision to be made as to whether to accept or reject a part.

Figure 7:
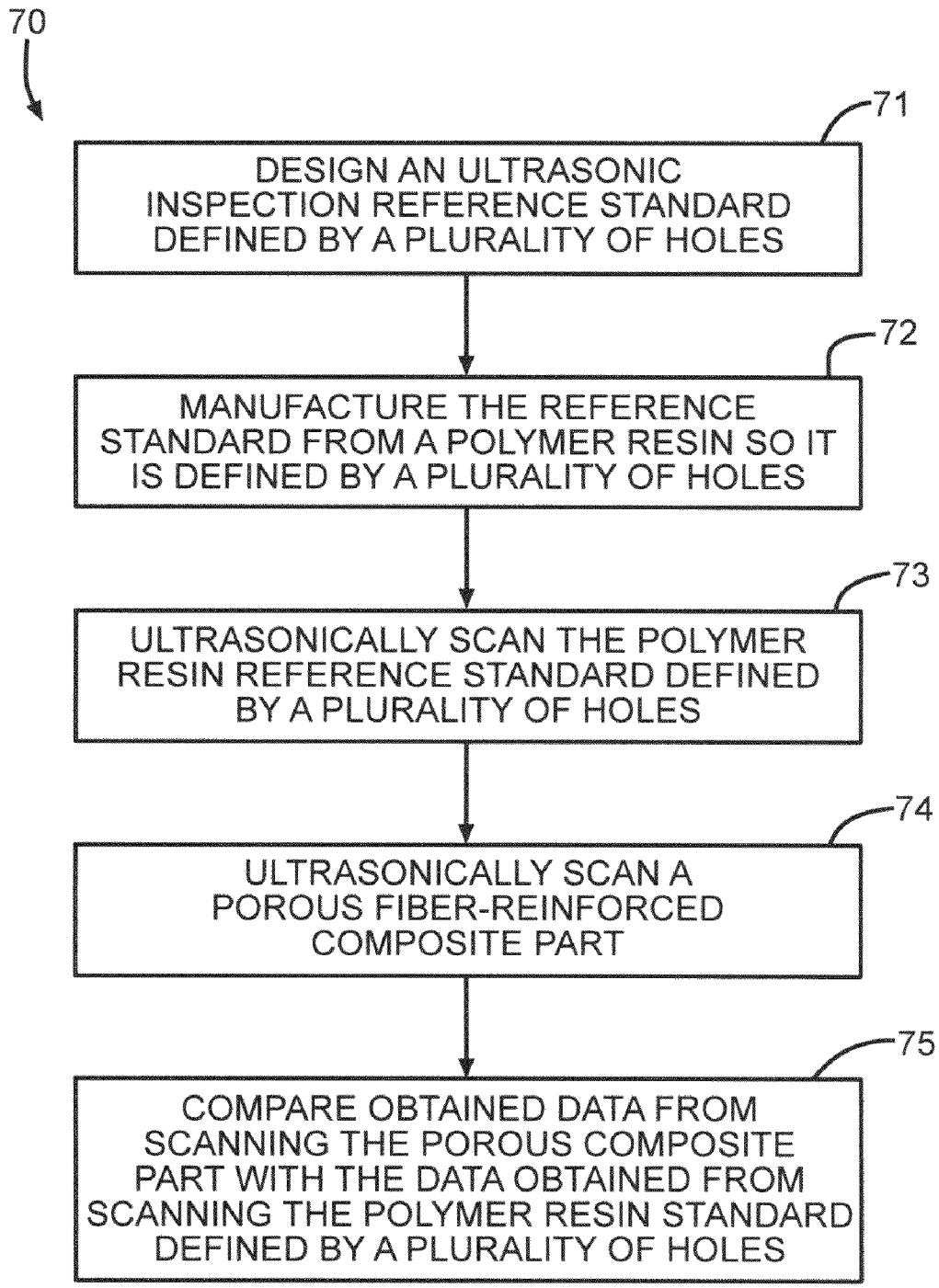
FIG. 7 is a flow chart of an ultrasonic inspection process for composite materials having porosity according to an embodiment of the present invention.

Referring to FIG. 7, an ultrasonic inspection process for composite materials having porosity 70 is illustrated according to an embodiment of the present invention. The ultrasonic inspection process 70 may include step 71 comprising designing an ultrasonic inspection reference standard, defined by a plurality of holes, according to a porous, fiber-reinforced composite part to be inspected. The porous, fiber-reinforced composite part to be inspected may comprise a graphite epoxy composite material having porosity. One or more of the sizes, locations, and spacing of the plurality of holes in the designed reference standard (or member) may be predetermined, prior to its manufacture, in order to provide the designed reference standard with the acceptable or respectable ultrasonic properties of the porous, fiber-reinforced composite part to be inspected. In such manner, the designed reference standard may comprise substantially the ultrasonic properties of a fiber-reinforced composite reference standard. Designing the ultrasonic inspection reference standard may include creating a 3D CAD model.

In step 72, the reference standard (also referred to herein as "member having at least one thickness") may be manufactured from a fiber-free polymer resin. The reference standard may be manufactured from a photo-polymer resin, utilizing stereo lithography, so that it is defined by a plurality of holes, in predetermined sizes, locations, or spacing, to mimic the acceptable or respectable ultrasonic properties of a porous, fiber-reinforced composite part. Next, in step 73, the polymer resin reference standard may be ultrasonic ally scanned using an ultrasonic inspection technique, such as pulse-echo and through-transmission. Then, in step 74, a porous, fiber-reinforced composite part may be ultrasonic ally scanned. As shown in step 75, the obtained data from scanning the porous, fiber-reinforced composite part is compared with the data obtained from scanning the polymer resin reference standard defined by a plurality of holes. Based on the data, a decision may be made as to whether to accept or reject the composite part.

By using a fiber-free polymer resin to manufacture the ultrasonic inspection reference standard, the reference standard may be manufactured at lower manufacturing cost, and in less time, using a method that does not require any tooling, as compared to existing fiber-reinforced composite reference standards. The manufactured ultrasonic inspection reference standard may substantially comprise the ultrasonic properties of a graphite-epoxy reference standard or other type of reference standard made of varying materials. In such manner, the manufactured ultrasonic inspection reference standard may replace a graphite-epoxy reference standard, or other type of fiber-reinforced reference standard.

Figure 8:
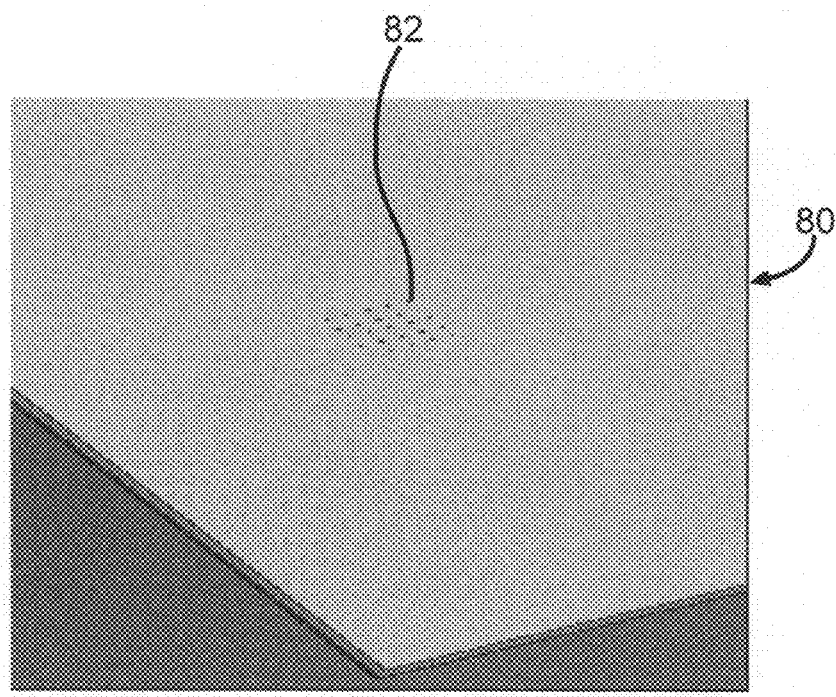
FIG. 8 is an isometric view of a thin resin laminate with small diameter holes produced using the stereo lithography process.
Figure 9:
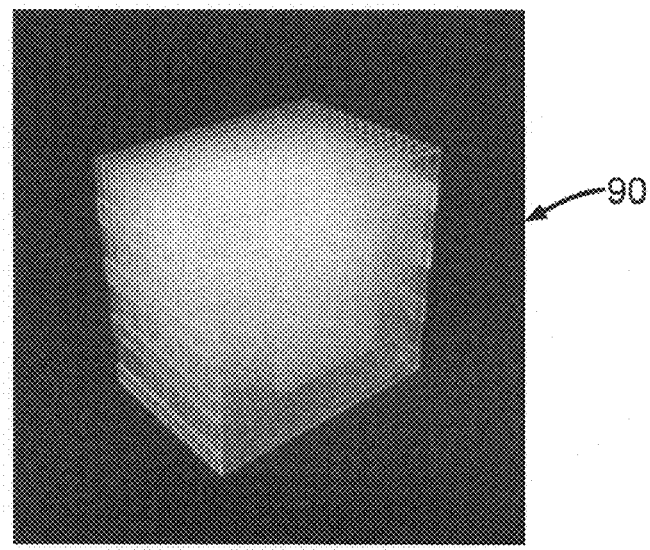
FIG. 9 is an isometric view of thin resin laminates produced using the stereo lithography process from a model.
Figure 10:
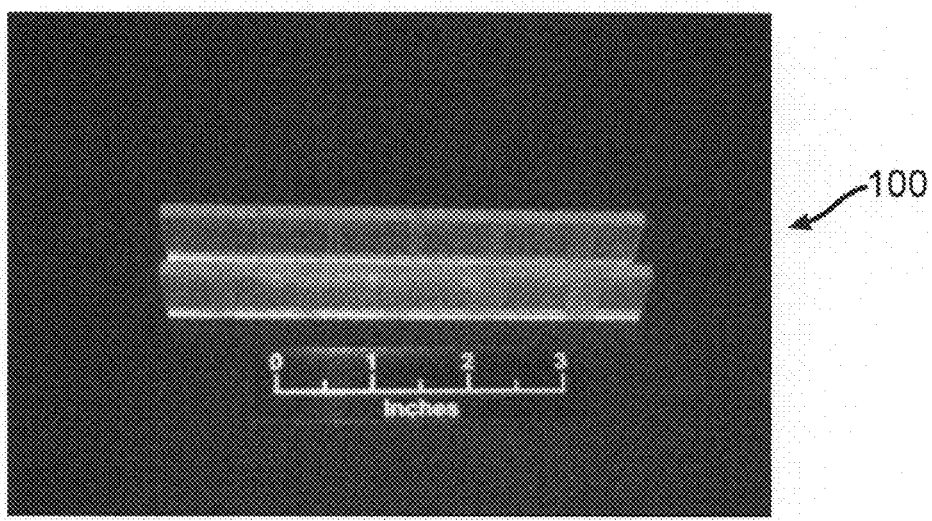
FIG. 10 is an isometric view of thick laminates with a multiple shaft hole pattern.
Figure 11:
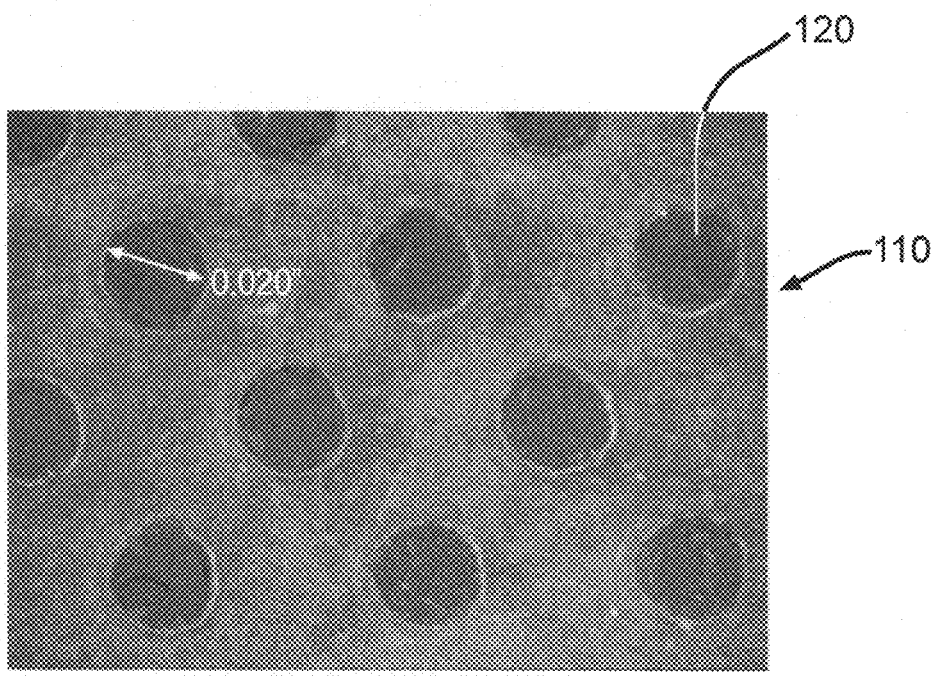
FIG. 11 is a high magnification photo of a hole pattern which shows the quality of holes that can be produced using the stereo lithography process.

FIGS. 8 and 9 depict thin resin laminates with small diameter holes produced using the stereo lithography process. FIG. 8 is an isometric illustration of the laminate 80, which is approximately 0.020" thick and has hole diameters 82 of approximately 0.020". FIG. 9 illustrates laminates 90 produced from a model using stereo lithography, with the laminate thickness to hole ratio much greater than one. FIG. 10 depicts thick laminates 100 with multiple shaft hole patterns. FIG. 11 is a high magnification photo 110 of a hole pattern showing the quality of holes 120 that can be produced using the stereo lithography process.

Figure 12:
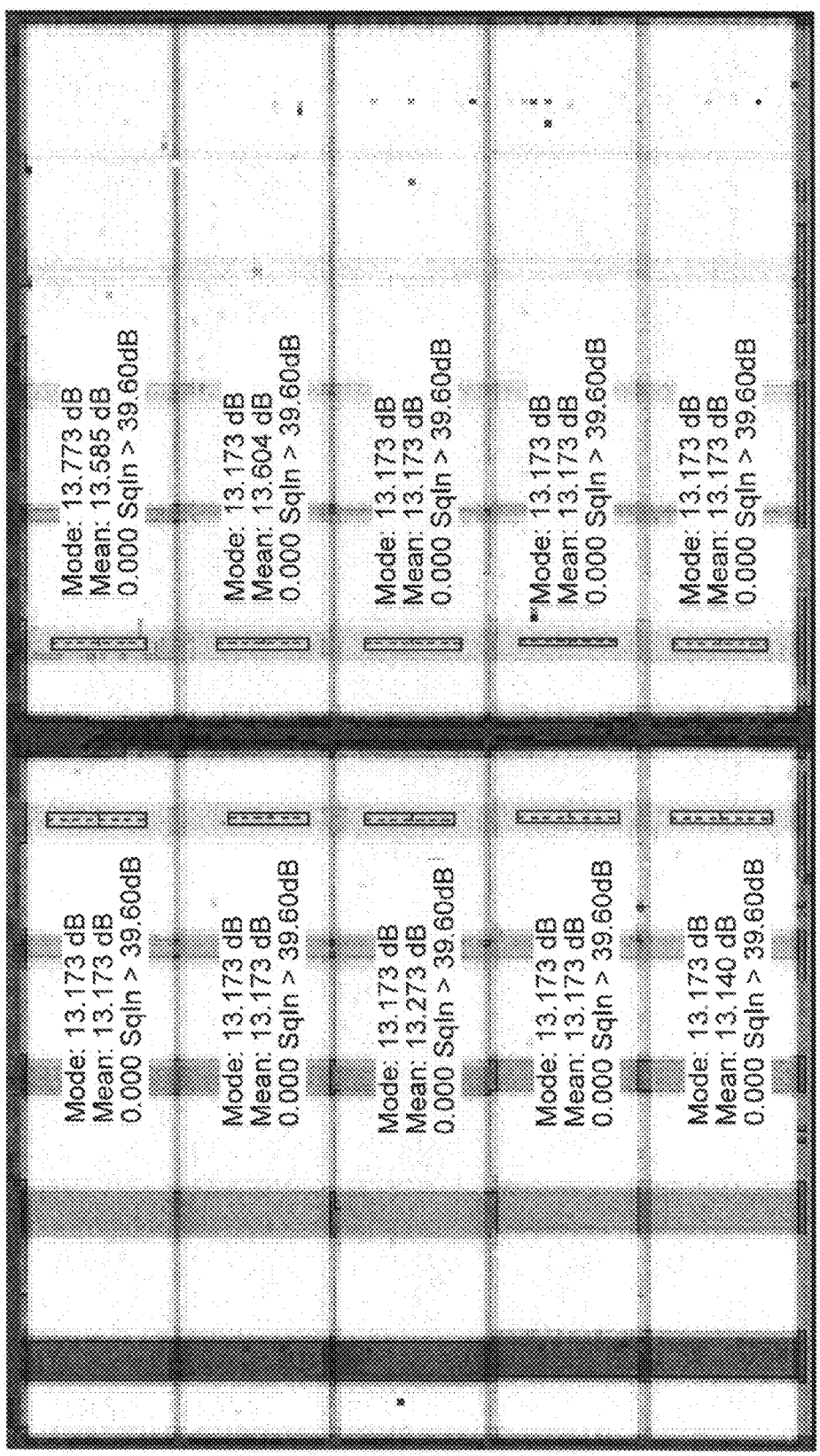
FIG. 12 shows the uniformity of the ultrasonic results for five samples produced using the stereo lithography process.
Figure 13:
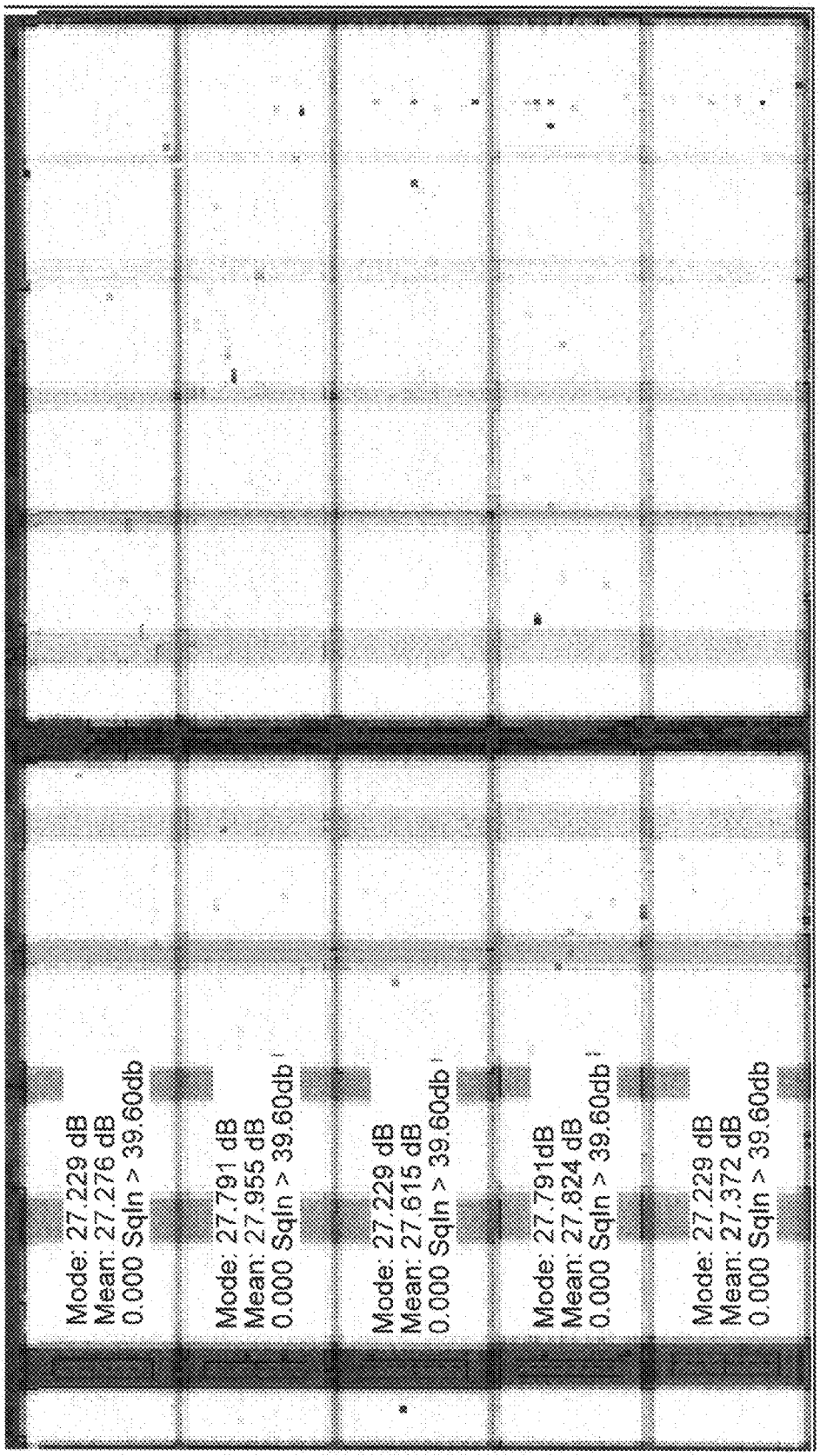
FIG. 13 shows the uniformity of the ultrasonic results for another five samples produced using the stereo lithography process.

Since the hole diameter and spacing of the plurality of holes in the manufactured reference standard may be accurately controlled by the three-dimensional model prior to using the stereo lithography process, there is a high degree of repeatability in the process. To illustrate this, a total of five samples were produced using the shaft hole pattern. Each sample was ultrasonic ally scanned to determine the acoustic repeatability of the samples. FIGS. 12 and 13 illustrate the ultrasonic results. The darker the color of gray the higher attenuation the ultrasonic sound experienced as it passed through the sample. The dark gray areas are of the hole patterns and the light gray areas are where the hole patterns do not exist. Histograms, indicated by the rectangles, were taken at several locations and compared to identical locations in the remaining samples. Both the mode and mean values were measured. The results indicate the hole patterns produced are ultrasonic ally uniform from sample to sample.

Using stereo lithography to produce holes in solid median is of value because manufacturing costs may be roughly ten percent of the traditional cost of manufacturing composite standards with similar holes/porosity. The ability to produce small diameter holes, in particular patterns, similar to naturally occurring porosity, makes this approach desirable in the manufacturing of pseudo porosity standards. Additionally, the nature of the manufacturing process, including its tailor ability and repeatability, may enable the production of multiple reference standards having substantially equivalent acoustic properties to allow inspection of porous, composite parts around the world. The cost of manufacturing and certification of prior art reference standards may be limited by utilizing the present invention to manufacture small diameter holes approaching the size of porosity typically seen in graphite epoxy. The process may become the foundation for the development of pseudo porosity standards to characterize ultrasonic equipment, and may replace current composite reference standards, such as graphite-epoxy reference standards. The invention may be used for ultrasonic inspection of porous, composite parts used in the aircraft airframe industry, both commercial and defense, and in other non-aircraft applications.

It should be understood, of course, that the foregoing relates to exemplary embodiments of the invention and that modifications may be made without departing from the spirit and scope of the invention as set forth in the following claims.

We claim:

1. An ultrasonic inspection reference standard for composite materials having porosity, comprising:
   a member having at least one thickness, said member being defined by a plurality of empty holes, wherein the empty holes ultrasonically mimic porous composite materials;
   wherein said member is manufactured from a fiber-free polymer resin.

2. The ultrasonic inspection reference standard of claim 1, wherein said polymer resin is a photo-polymer resin.

3. The ultrasonic inspection reference standard of claim 1, wherein said polymer resin is identical to the resin of a composite material to be inspected.

4. The ultrasonic inspection reference standard of claim 1, wherein said member comprises more than one thickness.

5. The ultrasonic inspection reference standard of claim 1, wherein said member is created using a 3D computer-aided-design model.

6. The ultrasonic inspection reference standard of claim 1, wherein said at least one thickness of said member is an equivalent thickness based on material properties of said composite material to be inspected.

7. The ultrasonic inspection reference standard of claim 1, wherein said member, including said plurality of empty holes, is manufactured using a stereo lithography process.

8. The ultrasonic inspection reference standard of claim 1, wherein said member contains the acceptable or respectable ultrasonic properties of said composite materials having porosity.

9. The ultrasonic inspection reference standard of claim 8, wherein one or more of the sizes, locations, and spacing of said plurality of empty holes is predetermined prior to manufacture of said member to provide said member with the acceptable or respectable ultrasonic properties of said composite materials having porosity.

10. The ultrasonic inspection reference standard of claim 1, wherein said member is manufactured using a method that does not require any tooling.

11. The ultrasonic inspection reference standard of claim 1, wherein said ultrasonic reference standard is for graphite epoxy composite materials having porosity.

12. An ultrasonic inspection reference standard for composite materials having porosity, comprising:
   a member having at least one thickness and a plurality of empty holes;
   said member being manufactured from a fiber-free polymer resin using stereo lithography;
   said member being adapted to contain the acceptable or respectable ultrasonic properties of a fiber-reinforced composite part having porosity.

13. The ultrasonic inspection reference standard of claim 12, wherein one or more of the sizes, locations, and spacing of said plurality of empty holes is predetermined prior to manufacture of said member to provide said member with the acceptable or respectable ultrasonic properties of said fiber-reinforced composite part having porosity.

14. The ultrasonic inspection reference standard of claim 12, wherein said member is manufactured from a photo-polymer resin.

15. The ultrasonic inspection reference standard of claim 12, wherein said member is adapted to substantially contain the ultrasonic properties of a graphite-epoxy reference standard.

16. The ultrasonic inspection reference standard of claim 15, wherein said member replaces said graphite-epoxy reference standard.

17. The ultrasonic inspection reference standard of claim 12, wherein said member is used to inspect a fiber-reinforced composite part of an aircraft airframe.

18. An ultrasonic inspection process for composite materials having porosity, comprising the steps of:
   manufacturing an ultrasonic inspection reference standard defined by a plurality of empty holes from a fiber-free polymer resin; and
   inspecting a fiber-reinforced composite part having porosity with an ultrasonic technique using said fiber-free polymer resin reference standard defined by the plurality of empty holes.

19. The ultrasonic inspection process of claim 18, further comprising the steps of:
   ultrasonically scanning said fiber-free polymer resin reference standard defined by the plurality of empty holes using an ultrasonic inspection technique;
   ultrasonically scanning said fiber-reinforced composite part having porosity using said ultrasonic inspection technique; and
   comparing data obtained from scanning said fiber-reinforced composite part having porosity with data obtained from scanning said fiber-free polymer resin reference standard.

20. The ultrasonic inspection process of claim 19, further comprising the step of deciding whether to accept or reject said fiber-reinforced composite part based on said data.

21. The ultrasonic inspection process of claim 18, further comprising the steps of:
   creating a 3D CAD model of an ultrasonic inspection standard; and
   creating a photo-polymer resin reference standard defined by a plurality of empty holes using stereo lithography.

22. The ultrasonic inspection process of claim 18, further comprising the step of using an ultrasonic technique selected from the group consisting of pulse-echo technique and through-transmission technique to scan said fiber-free polymer resin reference standard defined by the plurality of empty holes and to scan said fiber-reinforced composite part having porosity.

23. The ultrasonic inspection process of claim 18, further comprising the steps of:
   manufacturing a fiber-free photo-polymer resin reference standard defined by a plurality of empty holes using a stereo lithography process; and
   replacing a fiber-reinforced composite reference standard having porosity with said fiber-free photo-polymer resin reference standard defined by plurality of empty holes.

24. The ultrasonic inspection process of claim 23, further comprising the step of designing said fiber-free photo-polymer resin reference standard defined by a plurality of empty holes so that one or more of the sizes, locations, and spacing of the plurality of empty holes provides the fiber-free photo-polymer resin reference standard with substantially the ultrasonic properties of said fiber-reinforced composite reference standard having porosity.

* * * * *